United States Patent [19]

Prince et al.

[11] Patent Number: 4,695,454

[45] Date of Patent: * Sep. 22, 1987

[54] PROCESS FOR PREPARING HEPATITIS B SURFACE ANTIGEN CONTAINING PARTICLES IN NOVEL FORMS WHICH ARE HIGHLY IMMUNOGENIC

[75] Inventors: Alfred M. Prince, Pound Ridge; Kwang S. Kim, Staten Island, both of N.Y.

[73] Assignees: New York Blood Center, Inc., New York, N.Y.; Eugene Tech International, Inc., Allendale, N.J.

[*] Notice: The portion of the term of this patent subsequent to Jan. 27, 2004 has been disclaimed.

[21] Appl. No.: 718,248

[22] Filed: Apr. 1, 1985

[51] Int. Cl.⁴ .................... A61K 35/16; A61K 39/29
[52] U.S. Cl. .................................... 424/89; 435/236; 530/427; 530/806; 530/826
[58] Field of Search ............... 260/112 R, 112 B; 424/89, 88, 101; 435/236; 422/44; 530/427, 806, 826

[56] References Cited

U.S. PATENT DOCUMENTS

| 3,636,191 | 10/1969 | Blumberg et al. | 424/89 |
| 4,424,206 | 1/1984 | Ohmura et al. | 424/101 |
| 4,438,098 | 3/1984 | Tabor et al. | 424/89 |
| 4,440,679 | 4/1984 | Fernandes et al. | 424/101 |
| 4,565,697 | 1/1986 | Ohmura et al. | 424/101 |

FOREIGN PATENT DOCUMENTS 0159749 10/1985 European Pat. Off. .

OTHER PUBLICATIONS

Alfred M. Prince, Pro. Nat. Acad. Sci. (U.S.), 60:814–821 1968.
A. M. Prince, J. Vnek & B. Brotman, "An Affordable Multideterminant Plasma-Derived Hepatitis B. Virus Vaccine", 1984, IARC Scientific Publications, No. 63, pp. 355–372.

Primary Examiner—John Kight
Assistant Examiner—Nathan M. Nutter
Attorney, Agent, or Firm—Sprung Horn Kramer & Woods

[57] ABSTRACT

There is disclosed a process for producing a proteinaceous mass containing particles of HBsAg in a morphological form not found in nature while inactivating any live virus contained therein. The process comprises subjecting a concentrated mass thereof free of protein diluent or a stabilizer to a heat inactivation by heating the same while in a concentration of at least 1 mg/ml at a temperature of 101° to 105° C. for 1 to 5 minutes and thereafter cooling the so heated particles.

18 Claims, 8 Drawing Figures

PROCESS FOR PREPARING HEPATITIS B SURFACE ANTIGEN CONTAINING PARTICLES IN NOVEL FORMS WHICH ARE HIGHLY IMMUNOGENIC

BACKGROUND OF THE INVENTION

1. Field of the Invention

This invention relates to a solution or a suspension of particles useful as a vaccine or vaccine intermediate. More especially, this invention relates to a process for the production of hepatitis B surface antigen (HBsAg) carrying particles in novel forms which are highly immunogenic. Still more especially, this invention relates to a process for inactivating an antigen containing mass where the inactivation is performed employing heat on a highly concentrated antigenic mass, to wit, one which has not been diluted by the addition of a protein thereto such as albumin. This invention relates to a process for the production of such an antigenic composition and to the use thereof for immunizing animals, especially humans.

2. Discussion of the Prior Art

The relationship between what is now referred to as the hepatitis B surface antigen (HBsAg) and hepatitis B virus was definitively identified many years ago by Alfred M. Prince (Pro. Nat. Acad. Sci (U.S.) 60:814–821, 1968). This antigen is primarily located on proteins embedded in the membrane of lipoprotein particles having a particle size of approximately 18 to 24 nm and filaments of a similar diameter. These are now known to represent fragments of membrane similar to that which surrounds the virion of HBV, also known as the "Dane" particle.

Thereafter, a vaccine containing such particles was disclosed in U.S. Pat. No. 3,636,191 by Blumberg et al. Prince and others thereafter disclosed other hepatitis B viral vaccines containing membrane proteins derived from Dane particles and filaments. These Dane particles and filaments contained or were associated with the hepatitis B e antigen found in many chronic carriers of the hepatitis B virus.

Since the work described above was conducted, a vaccine against the hepatitis B virus was introduced in the U.S. containing HBsAg particles. This vaccine is produced by enzyme digestion of HBsAg containing particles derived from the plasma of chronically infected HBV carriers, more or less as described in U.S. Pat. No. 3,636,191, supra. This vaccine is prepared by a costly purification process which results in substantial losses of its immunogenicity. As a result, a relatively large dose of the resulting antigen (HBsAg) must be administered to assure an adequate immune response. Because of these factors, the vaccine has been available only at a relatively high cost, about $30.00 per dose or higher. Since an original injection and two boosters are required, it presently costs approximately $100.00 to become immunized against the hepatitis B virus in the United States, a cost that is not affordable in those parts of the world where the need for this vaccine is greatest.

It has become desirable, therefore, to provide a hepatitis B vaccine containing hepatitis B surface antigen in a substantially pure form having greatly increased immunogenicity so that much smaller, less costly, doses can be used. It is, of course, also essential that the infective virus present in the starting plasma has been completely inactivated so as to present no risk of infection.

Hepatitis B infection affects, for the most part, individuals residing in developing countries in Asia and Africa where limited funds are available for public health measures. It is mandatory in this twentieth century to provide such a vaccine for the protection of the hundreds of millions of people who are at risk of infection by hepatitis B virus, and as a consequence suffer the risk of subsequent development of cirrhosis and liver cancer, and to provide this at a cost that is affordable. In many parts of the developing world this necessitates that immunization must cost less than $1.00 per person, if the vaccine is to be used.

In co-pending application Ser. No. 656,833 now U.S. Pat. No. 4,639,371, there is disclosed a process for the production of a vaccine or vaccine intermediate characterized by HBsAG containing particles which have been to a large extent transformed into forms having a novel morphology, never found in nature. These forms have surprisingly enhanced immunogenicity.

According to experiments therein reported, a concentrated HBsAg containing mass is obtained by the steps of:

A. Precipitating HBsAg from blood plasma, e.g., human blood plasma containing the same, by contacting the same with polyethylene glycol to separate HBsAg from other blood serum proteins contained therein;

B. Affecting negative adsorption of such separated HBsAg on hydroxylapatite to further remove the bulk of serum proteins;

C. Subjecting the so adsorbed HBsAg to isopynic centrifugation to separate remaining intact Dane particles, and to further remove the remaining traces of contaminating serum proteins;

D. Subjecting the particles so separated by centrifugation to heat inactivation by heating them while at a concentration of 0.5–10 mg/ml at a temperature of 101° to 104° C. for 2 to 5 minutes and thereafter cooling the heated particles, e.g., by introducing them into an ice water bath.

It was believed, however, that the heat inactivation step of step D, supra, needed to be done in the presence of stabilizing concentration of proteins to avoid denaturation of the particles.

SUMMARY OF THE INVENTION

It has now been discovered, surprisingly, that the mass resulting from step C, supra, can be heat inactivated without addition of any stabilizers to of the HBsAg at all, i.e., without dilution of the HBsAg containing particles with material such as albumin. It has further been discovered that the heat inactivation not only provides an albumin free composition, but that the resultant composition is one in which the new morphological forms of the HBsAg are more readily visible by electron microscope.

It is believed that other viruses present in sera, e.g., human sera, can similarly be inactivated and as a result, concentrated antigenic compositions of other pathogens especially viruses can likewise be used as a vaccine or vaccine intermediate if the pathogen is heat inactivated according to the invention, i.e., without addition of a stabilizer such as sodium caprylate stabilized albumin. It should be noted that it is advantageous to provide a vaccine which is as pure as possible, i.e., a vaccine containing as few extraneous proteins, e.g., albumin, as possible.

Thus, broadly the invention relates to an improved process for the inactivation of a virus in a concentrated mass containing such virus and antigenic components thereof by heat inactivation wherein the concentrated mass is one obtained from serum containing said virus from which a substantial amount of serum proteins has been removed and the concentrated mass is subjected to heat inactivation without dilution thereof by a stabilizing, e.g., proteinaceous, diluent. Preferably, the entire process is performed such that no protein is added at any time during the concentration of the antigenic components or during the heat inactivation of the virus. Thereafter, if desired, the concentrated mass can be diluted such as with a protein, e.g., serum albumin, or with an adjuvant. It can also be diluted such as with saline to form a mass ready for administration or for further processing. The heat inactivation of the virus is effected by heating the concentrated mass containing the antigenic components, e.g., HBsAg particles, while at a concentration of 0.5–10 mg/ml at a temperature of 101° to 104° C. for 2 to 5 minutes and thereafter cooling the heated particles, e.g., by introducing them into an ice bath.

Overall, Hepatitis B vaccine is prepared in accordance with the present invention by the steps of:

A. Precipitating HBsAg from blood plasma, e.g., human blood plasma containing the same, by contacting the same with polyethylene glycol to separate HBsAg from other blood serum proteins contained therein;

B. Affecting negative adsorption of such separated HBsAg on hydroxylapatite to further remove the bulk of serum proteins;

C. Subjecting the so adsorbed HBsAg to isopynic centrifugation to separate remaining intact Dane particles, and to further remove the remaining traces of contaminating serum proteins;

D. Subjecting the particles so separated by centrifugation without dilution of the same by a protein to heat inactivation by heating them while at a concentration of 0.5–10 mg/ml at a temperature of 101° to 104° C. for 2 to 5 minutes and thereafter cooling the heated particles, e.g., by introducing them into an ice water bath.

In accordance with the present invention, steps A–C are conducted such that the mass to be treated contains at least 95% and preferably 99% by weight HBsAg containing particles, based on the total weight of protein. No diluent such as sodium caprylate treated albumin is added to the composition to stabilize the same during heat inactivation. Thus, the process of heat inactivation is carried out in the absence of a stabilizer, especially in the absence of other blood plasma proteins.

The heat inactivation step is preferably carried out at 101° to 104° C. by passing the undiluted purified particle solution resulting from step C through a 2 mm diameter tube, (e.g., brass or stainless steel etc.) immersed in a 101° to 104° C. heated medium, (e.g., oil bath) for a total dwell time of 2.5 to 6.0 minutes. It should be recognized that in employing the procedure of the invention some time is required to heat the solution inside the tubing up to 101° to 104° C. and hence, the "dwell total time" will be longer than the time at which the solution is actually heated at 101° to 104° C. The difference will, of course, depend on flow rate.

It should be recognized that continuous flow flash heating must be carried out at elevated pressure to prevent vaporization of the solution when it is brought to temperatures above 100° C. This is easily accomplished by the use of a high pressure liquid chromatography pump and a hydrostatic pressure head emanating from the receiving vessel.

Optionally, an additional inactivation can be carried out by treating the purified antigen from step C with a detergent such as Tween 80, e.g., adding an equal volume of a solution of 2% Tween 80 in water. This treatment further enhances the safety of the vaccine. It is preferred, however, to eliminate the detergent treatment as the resultant product is more immunogenic if the inactivation procedure is carried out without detergent treatment.

Following the flash heat inactivation step, the recovered purified and virus inactivated particle solution can be adjuvanted by adsorption to aluminum phosphate or aluminum hydroxide gels, if desired. For use in tropical countries, it may be desirable to lyophilize the vaccine prior to addition of alum gels, and to add the latter after rehydration, if desired.

Thereafter, it is worked up as a final vaccine by dilution with a physiologically acceptable medium, such as, 0.15 Molar NaCl.

In the final vaccine the HBsAg containing protein concentration is 0.1 to 10 micrograms per ml. A suitable dose for injection depends upon the age of the recipient. For an adult male, a typical dose has between 1 and 10 micrograms of HBsAg, and can be introduced intramuscularly, subcutaneously or intradermally.

BRIEF DESCRIPTION OF DRAWINGS

Referring to the drawings appended hereto.

DETAILED DESCRIPTION OF THE INVENTION

Hepatitis B surface antigen is purified from plasma by successive steps of polyethylene glycol precipitation, hydroxylapatite absorption and isopycaic centrifugation in a potassium bromide gradient as described below.

Thereafter, the composition is subjected to filtration through a 0.22 micron filter and, without addition of a stabilizer or protein diluent, subjected to heat inactivation by heating the same at 101° to 104° C. for 1 to 15 minutes, optionally for 2 to 5 minutes while the composition is passed through a 0.1 to 10 mm, optionally 1 to 3 mm diameter stainless steel tubing resting in an oil bath maintained at 102° to 105° C., under pressure, as described above. The pressure must be sufficient to prevent boiling, i.e., 800 to 1000 mm Hg, especially 900 to 1000 mm Hg.

The so heated mass is then cooled, such as by collection of the heated solution into a vessel resting in an ice water bath. Generally, cooling to 2°-4° C. is affected within 5 minutes following cessation of the heat treatment. However, it may be desired to pass the solution through a second coil in a bath set at any derived temperature between 20° and 100° C., especially 75°-90° C. to achieve optimal results.

The purified and flash heat inactivated HBsAg containing material is then adjuvanted suitably by the use of an aluminum phosphate adjuvant. Generally, a presterilized aluminum phosphate is added to the inactivated diluted antigen under sterile conditions to provide 0.3 to 0.6 mg aluminum phosphate per ml of diluted antigen. Thereafter, the adjuvanted composition is sterile filled into suitable containers. The final containers may be further held for 10 hours at 65° C. ("pasteurization") as an additional sterilization step to further assure safety of the final product. The vaccine is maintained at a temperature of 2° to 6° C. for up to 3 years prior to use in immunization.

Figure 1:
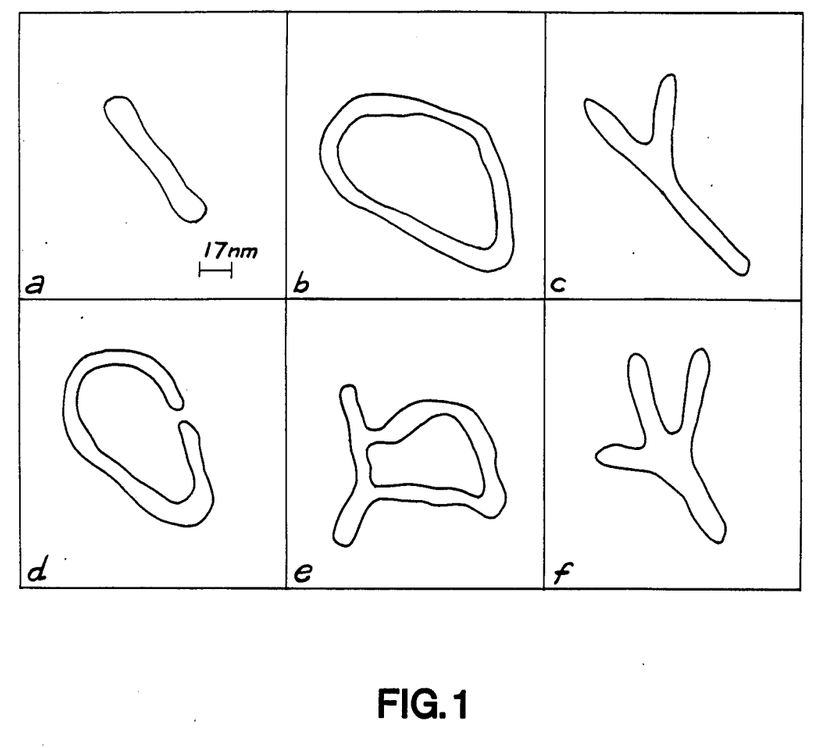
FIG. 1 is a schematic illustrating the filamentous forms produced from small spherical particles by flash heating: a. linear filament; b. closed circular or ring shaped filament; c. branched filament; d. open circular filament; e. branched circular filament; f. multiple branched filament.
Figure 2:
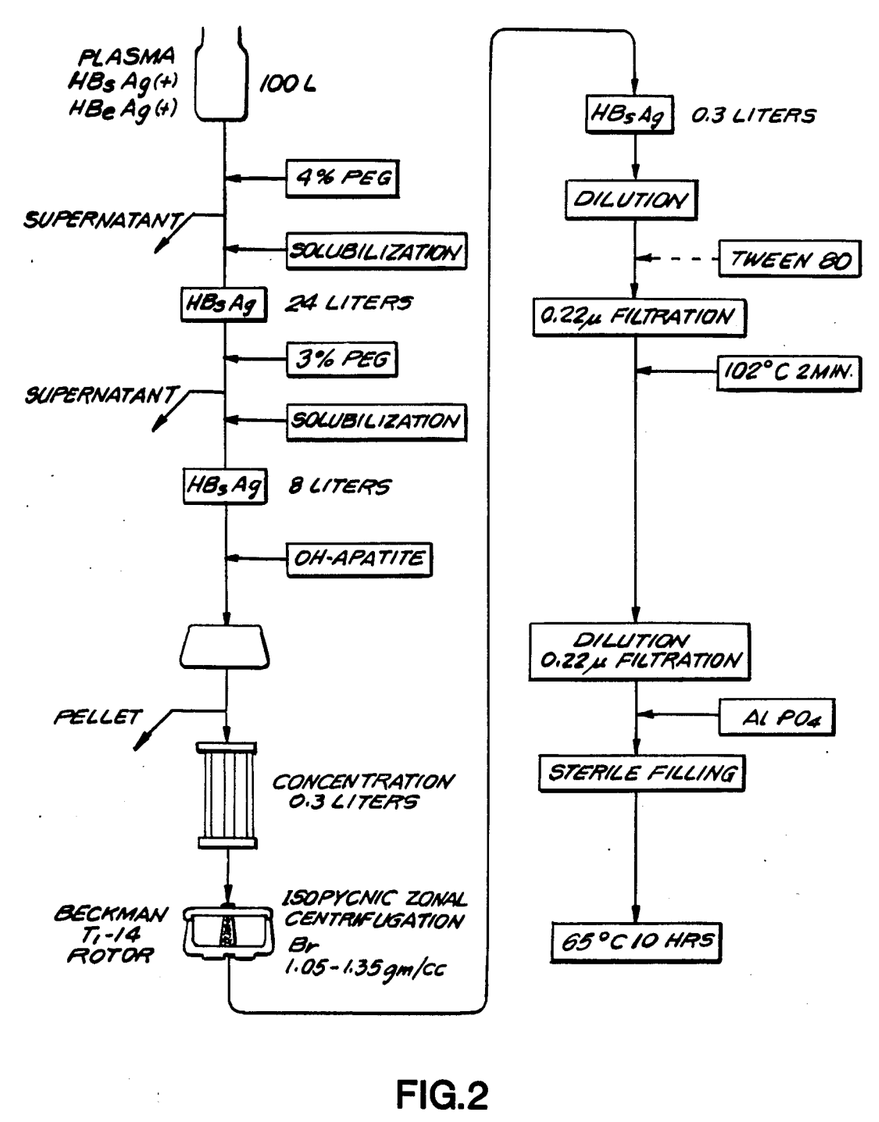
FIG. 2 is a flow diagram showing a method for the preparation of the vaccine according to the invention.

As a result of purifying the HBsAg in the manner described above and subjecting the undiluted HBsAg containing particles to the described heat treatment, unusually shaped HBsAg containing particles of the type formed pursuant to Ser. No. 656,833 now U.S. Pat. No. 4,639,371, are also realized but, of course, without the co-presence of the stabilizer. Such process not only avoids the cost entailed in the addition of a stabilizer/diluent, but it permits one to more readily monitor the system to ensure that these new morphological forms are produced as with the process of the invention the new morphological forms are more readily visible under electron microscope. Whereas the initial HBsAg containing particles are generally spherical and largely of a size of 18 to 24 nm (FIG. 3), particles derived by the process of the invention are predominantly transformed into polymorphous filaments, as seen especially in FIGS. 1,4 and 6. Especially remarkable are the heretofore unseen filaments, as seen in FIGS. 4 through 7, especially FIG. 5. Such filaments which contain HBsAg antigenicity are characterized by being branched, or ring shaped. They can be curvilinear or rectilinear in configuration. Generally speaking, the filaments have a length of at least 50 nm and are generally between 100 and 1000 nm.

When the filamentous structures are branched, they are branched with a structure having a length of at least 50 nm and frequently 100 to 300 nm. Some of the filaments obtained by the process of this invention have at least three branches per filament structure and have an irregular configuration, the minimum length of which is at least 100 nm and is preferably 200 to 1000 nm.

Referring to the electron micrographs of FIGS. 4 through 7, it will be observed that the HBsAg containing particles of the invention include ring shaped particles, branched filaments and linear filamentous particles, as well as spherical 16-25 nm HBsAg particles.

The morphological forms include ring shaped particles which have filamentous portions protruding therefrom. These filamentous particles usually have a length of at least 50 nm and generally are 100 to 300 nm in length.

When detergent treatment is used the non-branched filaments can be further characterized by a density at 20° C. of between 1.210 and 1.230 Gm/cc (mean 1.224 Gm/cc) and, thus, are distinguished from non-branched filaments seen in plasma of some chronic HBsAg carriers who have so called Dane particles and/or associated filaments. The latter have a mean density of 1.200.

The "ring shaped" particles include those which form a substantially perfect circle or ring as well as others which substantially enclose a region. The area defined by the surrounding HBsAg containing mass can be any shape including elliptical and donut-shaped, i.e., it can have a regular or irregular configuration.

The morphological forms observed differ dramatically from previously described micellar particles. The latter are characterized by a central hub composed of hydrophobic ends of polypeptide chains, the hydrophilic portions of which extend towards the surface of roughly spherical particles whereas the filaments prepared according to the invention are not connected to a central hub. Some filaments are in the form of irregular, rings which themselves can have protruding filaments. However, normally there are no more than three, usually two or only one such protruding filaments. Of course, the particles of the invention do not have a dense compacted core with outwardly projecting filaments.

The invention has been described with particular references to inactivating HBV en route to a Hepatitis B vaccine. The procedure is, however, useful in the manner described to inactivate other live viruses in concentrated mass containing the same and antigenic components of said viruses including in particular lipid coated virus, retro viruses, adenoviruses, herpes viruses, pox viruses, reoviruses, myoxoviruses, measles and mumps viruses, and leukoviruses. Specific viruses which can be inactivated in antigenic masses en route to vaccine preparation according to the invention include, influenza viruses including the various strains thereof, e.g., Strain X-31 and Japan strain, Epstein-Barr, polio, diphtheria, avian sarcoma, fowl plague, foot and mouth disease, cholera, Hepatitis A, HTLV-3, rabies and small pox.

In order to more fully illustrate the invention and the manner of practicing the same, the following examples are presented:

EXAMPLE 1

Pooled plasma containing both HBeAg and HBsAg obtained from chronic HBsAg carriers is adjusted to pH 4.6 and clarified at 10,000 RPM in a Westphalia continuous flow centrifuge. The clarified supernatant is adjusted to final concentration 4% PEG 6000 at 4° C. and stirred for 20 minutes. The precipitate is recovered by sedimentation for two hours without centrifugation and is solubilized in 1/5th of the original volume with distilled water by adjusting the pH to 7.5-8.0. The pH is then lowered to 5.0 and the resulting precipitate is recovered by centrifugation. The pH of the supernate is then adjusted to 4.6 and PEG is added to a final concentration of 3%.

After sedimentation overnight at 4° C., the precipitate is redissolved by neutralization and the suspension clarified after lowering the pH to 5.0 as before. The material is adjusted to pH 6.8 and after addition of 0.005 M phosphate buffer further purified by 2-3 consecutive adsorptions with equal volumes of packed hydroxylapatite. Subsequently, the hydroxylapatite sediments are washed with 0.02 and 0.05 M phosphate buffer. Finally, the original supernatants and the washes of the hydroxylapatite sediments are pooled, clarified by centrifugation and concentrated to about 0.3% of starting plasma volume with an Amicon hollow fiber cartridge. The concentrated HBsAg is then adjusted to a density of 1.25 gm/ml with solid KBr and dynamically loaded under a linear 1.05 to 1.2 g/ml KBr gradient over a 1.3 g/ml cushion into a Beckman Ti-14 rotor. The gradient is centrifuged for 18 hours at 28,000 rpm and fractionated by pumping water into the center of the rotor. Fractions corresponding to densities between 1.17 and 1.22 g/ml are pooled.

The purified antigen is adjusted to a concentration of 1 mg/ml (based on $OD_{280}$, $E_1cm$ 0.1%=3.73), and filtered through a 0.22 micron Millipore filter. Thereafter, the purified antigen is passed under 950 mm Hg pressure through a 2 mm diameter stainless steel coil suspended in an oil bath maintained at a temperature of 102° C. at a rate such that the material is held at 102° C. for 2 minutes. This requires a total dwell time of 2 minutes, 40 seconds. Following dilution, the resultant composition is adjuvanted with sterile aluminum phosphate. The final alum absorbed vaccine may be further treated for 10 hours at 65° C. as an additional virus inactivation step.

COMPARATIVE EXAMPLE 2

Figure 3:
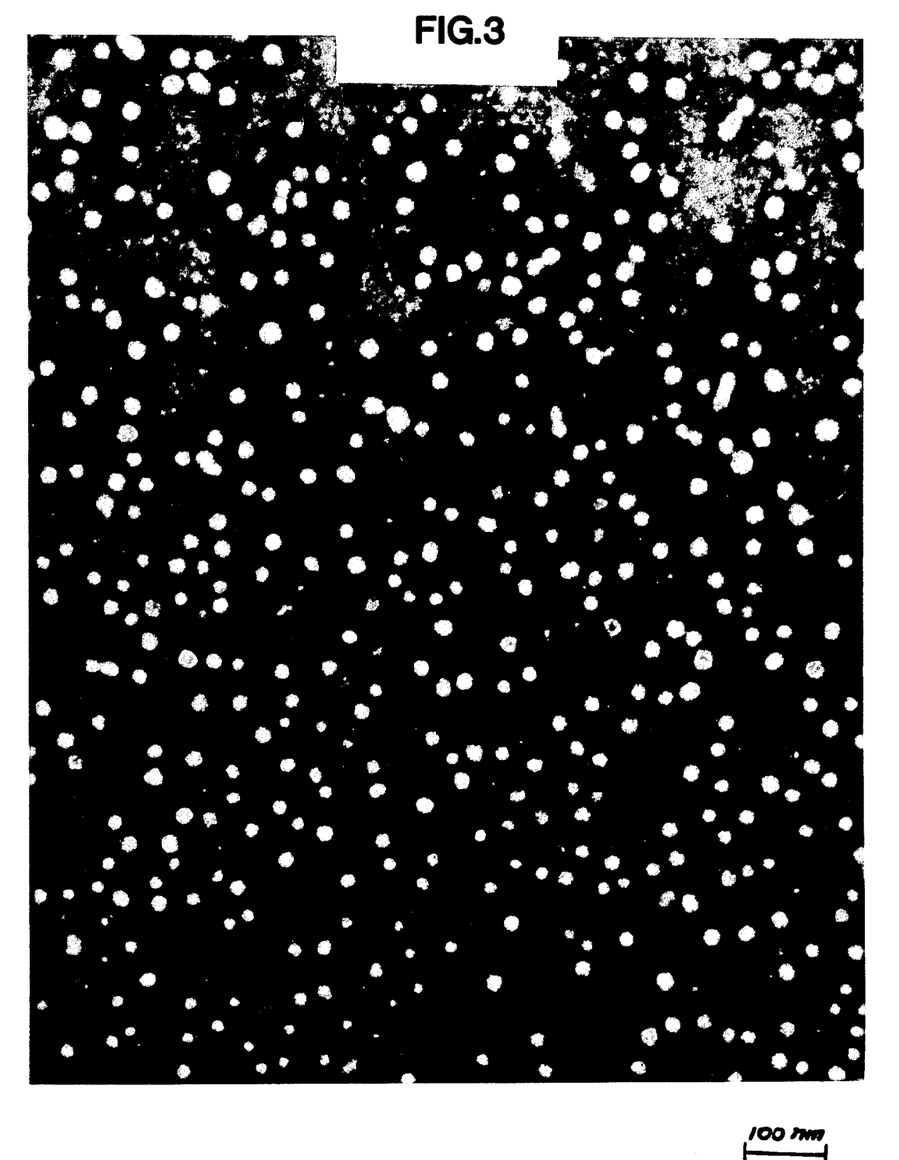
FIG. 3 is an electron micrograph of phosphotungstic acid negatively stained HBsAg containing particles obtained following steps A–C above, which were not subjected to the flash heat treatment of the invention and contain HBsAg particles in the form predominantly of 18 to 24 nm spherical particles.

The procedure of Example 1 is repeated substantially except for the heat inactivation step at 102° C. and the steps following. There is obtained a HBsAg containing mass having a protein concentration, as expressed in Example 1, of 1.18 mg/ml. The purity of the HBsAg is equal to or greater than 95%, based on gel diffusion study with polyvalent and monovalent anti-human serum protein anti-sera. The composition is, therefore, largely free of detectable amounts of human serum proteins. A portion of the sample is subjected to electron microscopy at 195,000 X magnification after negative staining with 2% phosphotungstic acid. An electron micrograph of this sample is shown in FIG. 3.

EXAMPLE 3

Figure 4:
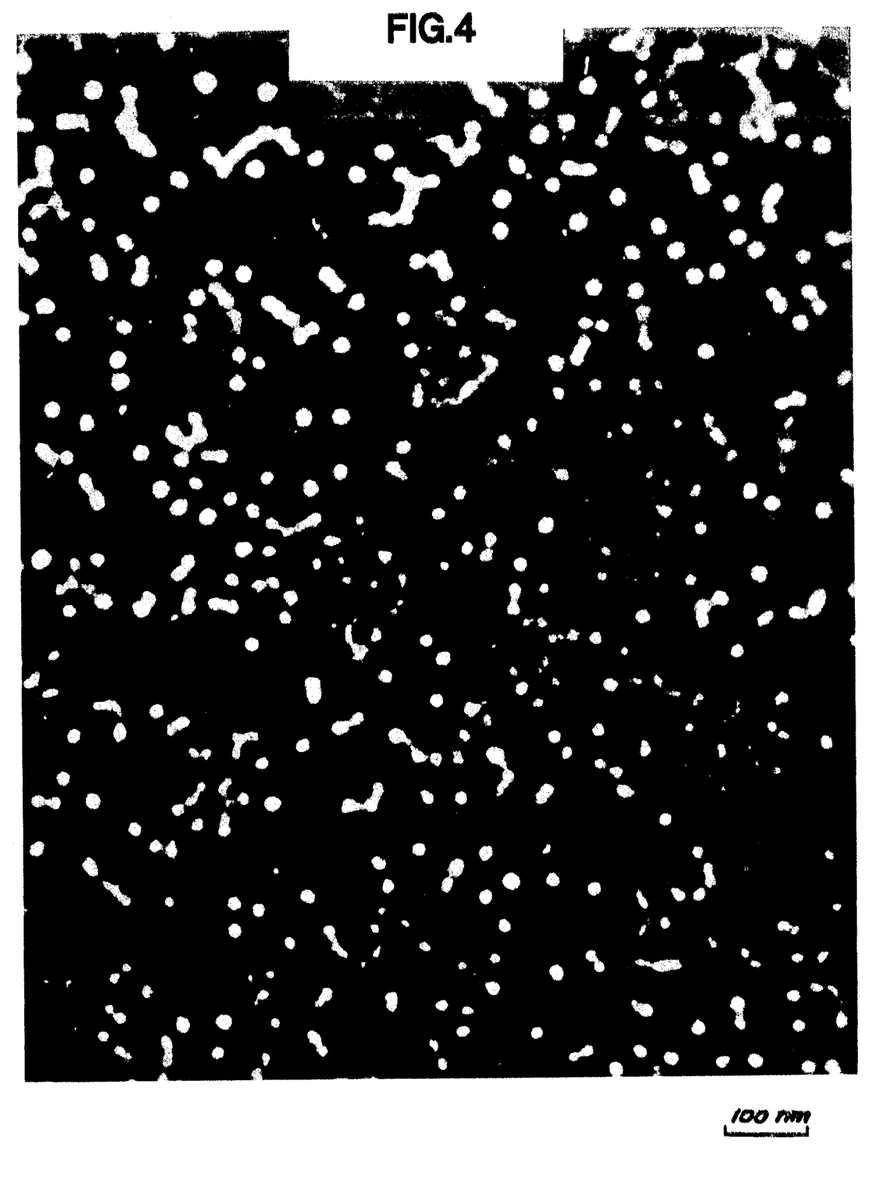
FIG. 4 is an electron micrograph, similar to FIG. 1, showing the form of the HBsAg containing particles when subjected to the heat treatment, showing the particles transformed into linear, branched and circular filamentous forms.

A portion of the sample described in Example 2 is thereafter subjected to a heat treatment by exposing it to 102° C. by passage through a 2 mm diameter stainless steel tubing immersed in an 102° C. oil bath for a total dwell time of two minutes forty seconds. Forty seconds is required to reach the 102° C. temperature. Hence, the protein composition is heated at 102° C. for about two minutes. The sample becomes slightly opalescent, indicative of some aggregation. A portion of the sample is negatively stained and electron microscopic photographs are taken thereof. As shown in FIG. 4, linear, branched generally circular filamentous forms of surface antigen particles appear after heating. These particles are not present in the original preparation. These particles result from actual membrane fusion rather than simple aggregation since even 30 minutes of exposure to ultrasonication does not affect their morphology.

To determine the relative immunogenicity of the filamentous and spherical particles, these are partially separated from each other by centrifugation.

EXAMPLE 4

The heated preparation of Example 3 is centrifuged at 8,000 g for 20 minutes and separated into a supernatant fraction which is furthered filtered through a 0.22 micron Millipore membrane after addition of 50 μl/ml of Tween 20 to reduce losses from filtration. A portion of this supernatant fraction is negatively stained and subjected to electron microscopy resulting in the electron micrograph of FIG. 5.

EXAMPLE 5

Figure 5:
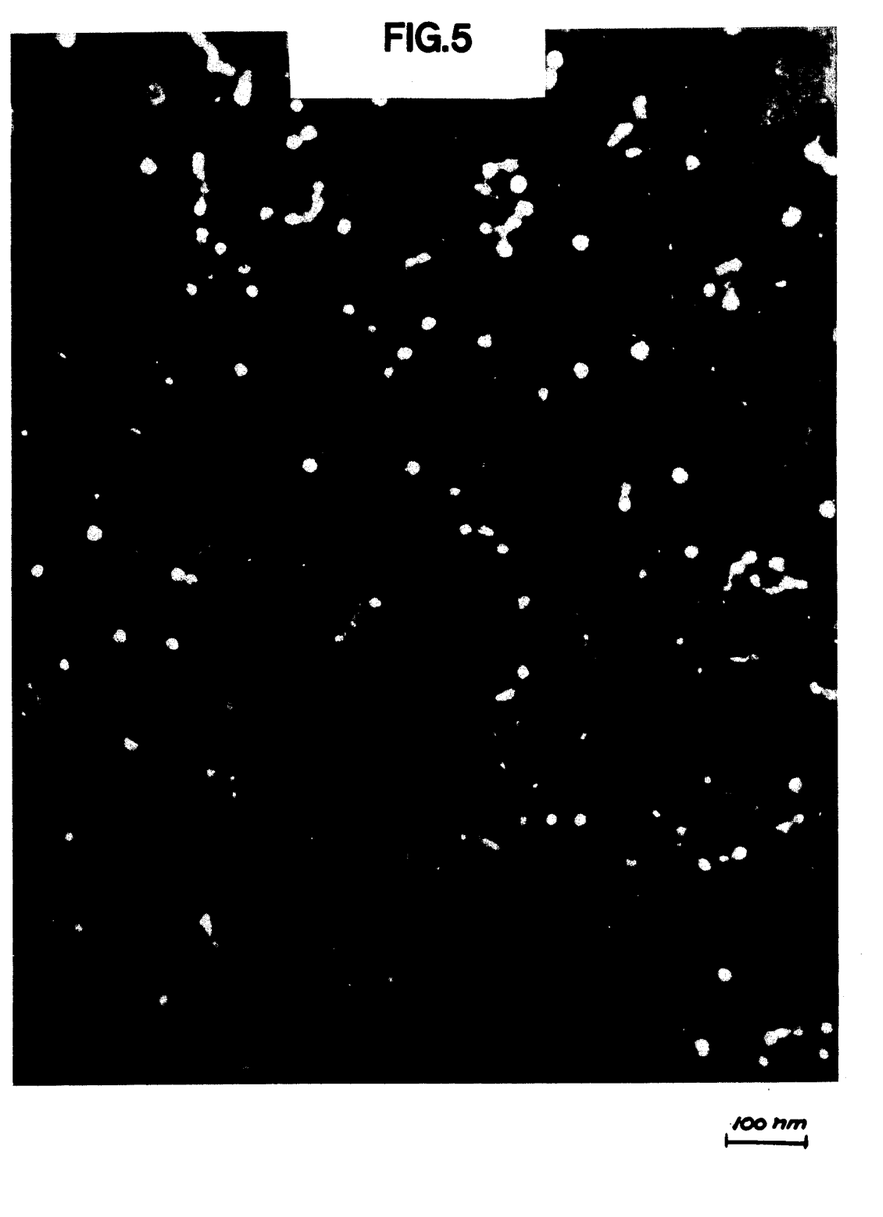
FIG. 5 is an electron micrograph, similar to FIGS. 3 and 4, of a supernatant fraction obtained after centrifuging the solution shown in FIG. 4 for 20 minutes at 8000 g and filtering the resultant supernatant.

The sediment from the filtration of Example 4 is resuspended in isotonic saline to original volume and, following negative staining, subjected to electron microscopy to produce the electron microscopic photograph of FIG. 5.

EXAMPLE 6

Flash Heat Inactivation in the Presence of Albumin

Figure 7:
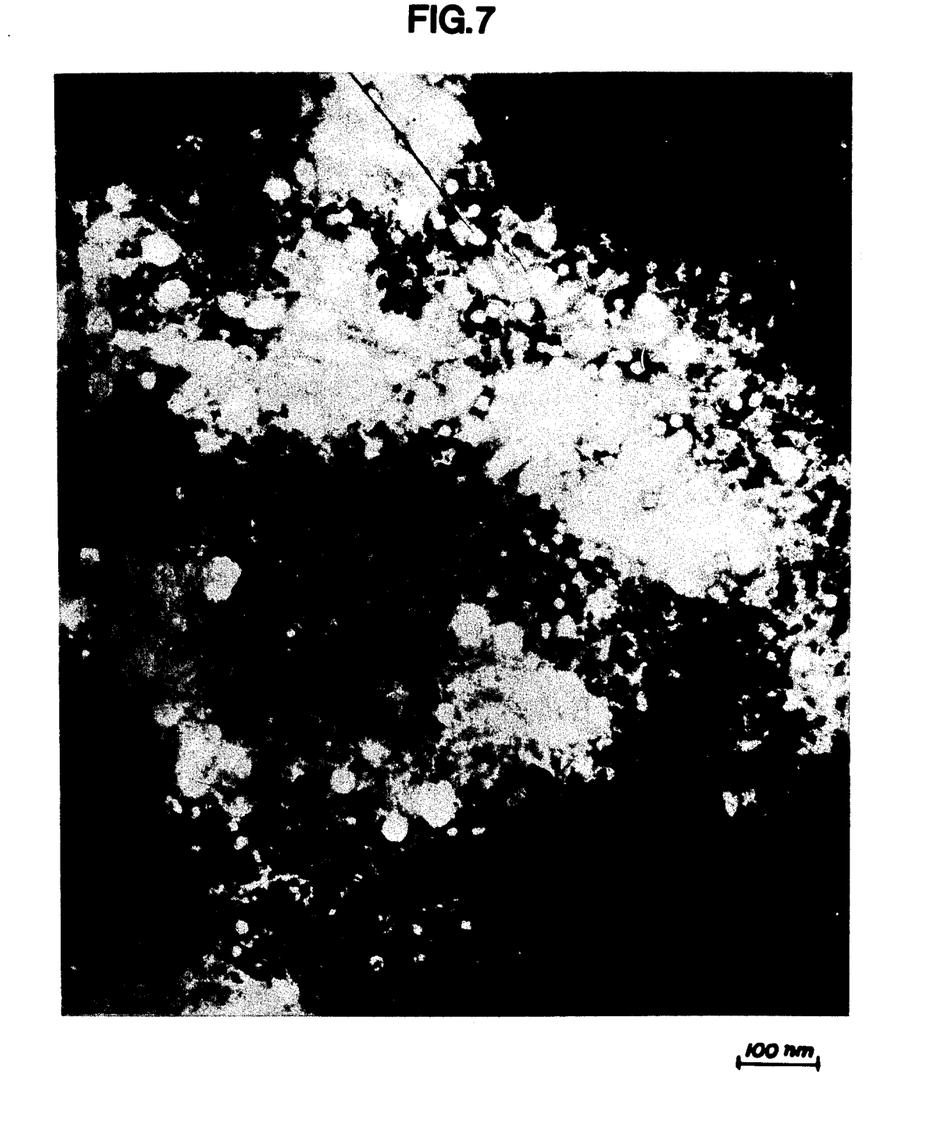
FIG. 7 is an electron micrograph similar to FIGS. 3 through 6, showing HbsAg containing particles prepared by this invention wherein the HBsAg particles were flash heat treated in the presence of 3 mg/ml of sodium caprylate treated serum albumin. The same morphological structures were obtained, but they are not as readily visible in the electron micrographs due to the co-presence of the sodium caprylate treated serum albumin.

A preparation was flash heated as described in Example 3 in the presence of 3 mg/ml of human serum albumin, stabilized by sodium caprylate. Polymorphic filamentous forms were again produced (FIG. 7).

EXAMPLE 7

Preparation of Adjuvanted Proteinaceous Compositions 30 micro liters of the composition of Examples 2 and 3, 40 micro liters of the composition of Example 4 and 90 micro liters of the composition of Example 5 are added each to 10 ml of sterile normal saline to yield an estimated 4 micro grams per ml based on $OD_{280}$. This is recognized to be an approximate estimation of protein concentration due to the opalescence resulting from the heating process. More exact protein contents of these samples are obtained by the BIORAD protein assay. The solutions are adjusted with equal volumes of aluminum phosphate gel (1.2 mg/ml), prepared by the Rijks Inst. voor de Volksgesundheid of Bilthoven, Holland, to yield an estimated 1 micro gram/0.5 ml dose adsorbed to 0.3 mg alum phosphate gel.

Dilutions in saline containing 1/4 and 1/16 the amount of each antigen are similarly adsorbed to alum adjuvant as above to give estimated doses of 0.25 and 0.6 micro grams. A control is also prepared with saline instead of antigen solution.

Inoculation of Mice

Groups of 20 female ICR Swiss mice weighing 20-22 grams are inoculated intraperitoneally with 0.5 cc of the various preparations. Thus, each sample is inoculated into 60 mice, 20 receiving each of the three dilutions. Ten mice received the control adjuvant.

All mice are bleed by cardiac exsanguination. The blood is collected into individual tubes, allowed to clot at room temperature and held over night at 4° C. prior to recovery of serum from the centrifuged (3,000 rpm, 15 min) clots.

Each serum is tested by a quantitative parallel line radioimmunoassay using AUSAB® test kits (Abbott Laboratories, Chicago, Ill.), in comparison to the WHO International HBIG standard containing 100 international units (IU) per ml. Samples giving radioactivity greater than that within the linear curve relating dilution and counts per minute (CPM) minus negative control mean CPM were retested at 1:10 and 1:100 dilutions. HBsAg antigenicity of samples was estimated by a parallel line radioimmunoassay using AUSRIA® test kits (Abbott Laboratories, North Chicago, Ill.) in comparison to a provisional HBsAg/ad standard provided by the U.S.F.D.A. Results obtained with this standard are identical to those which have been independently obtained using the German National HBsAg/ad standard.

Figure 6:
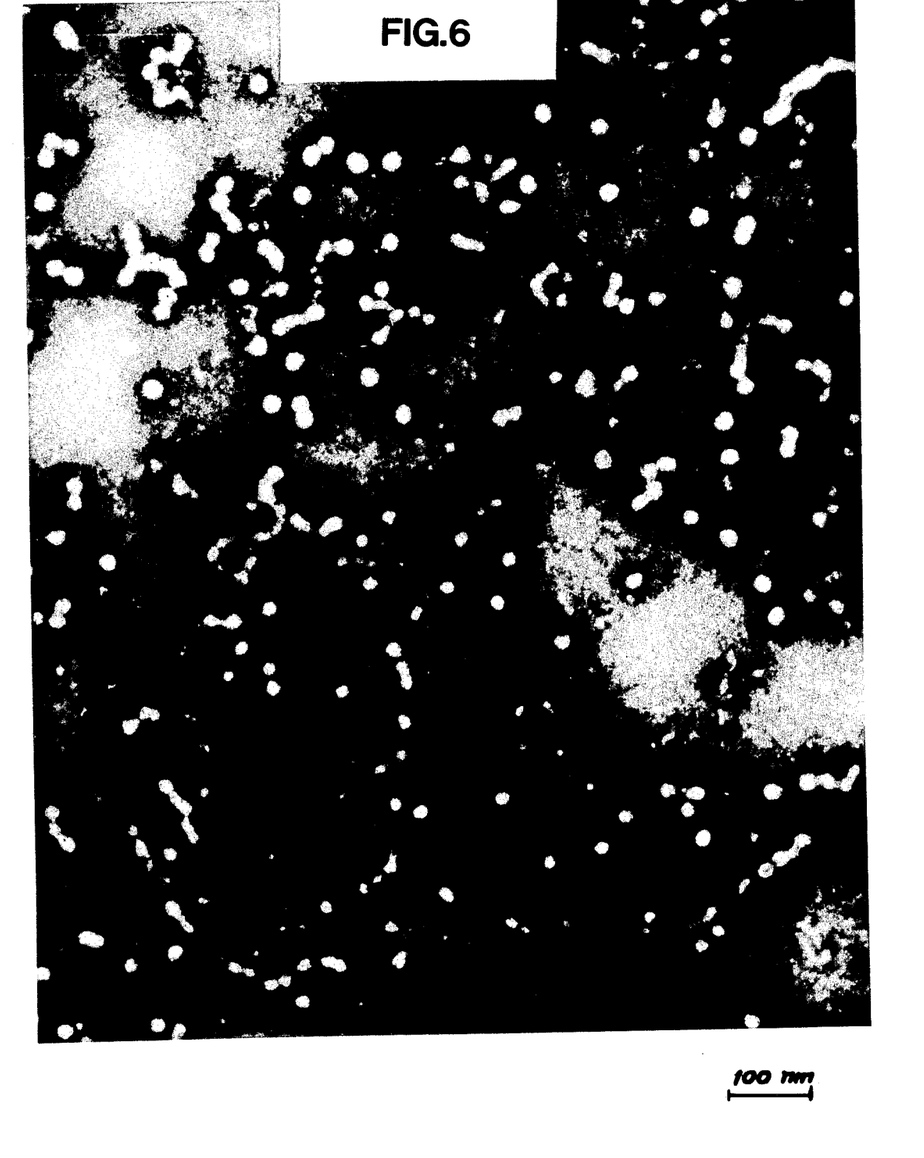
FIG. 6 is an electron micrograph similar to FIGS. 3 through 5, of the sediment obtained from centrifugation for 20 minutes at 8000 g resuspended in isotonic saline to original volume.

Table 1 below sets forth the protein content and the antigenicity of the different samples of Examples 2 through 5 and the ratio between these, i.e., "specific antigenicity". It may be seen that heating reduces the specific antigenicity by about 50%. This is particularly evident for Example 5 which has enriched filamentous forms, as seen by FIG. 6.

Figure 8:
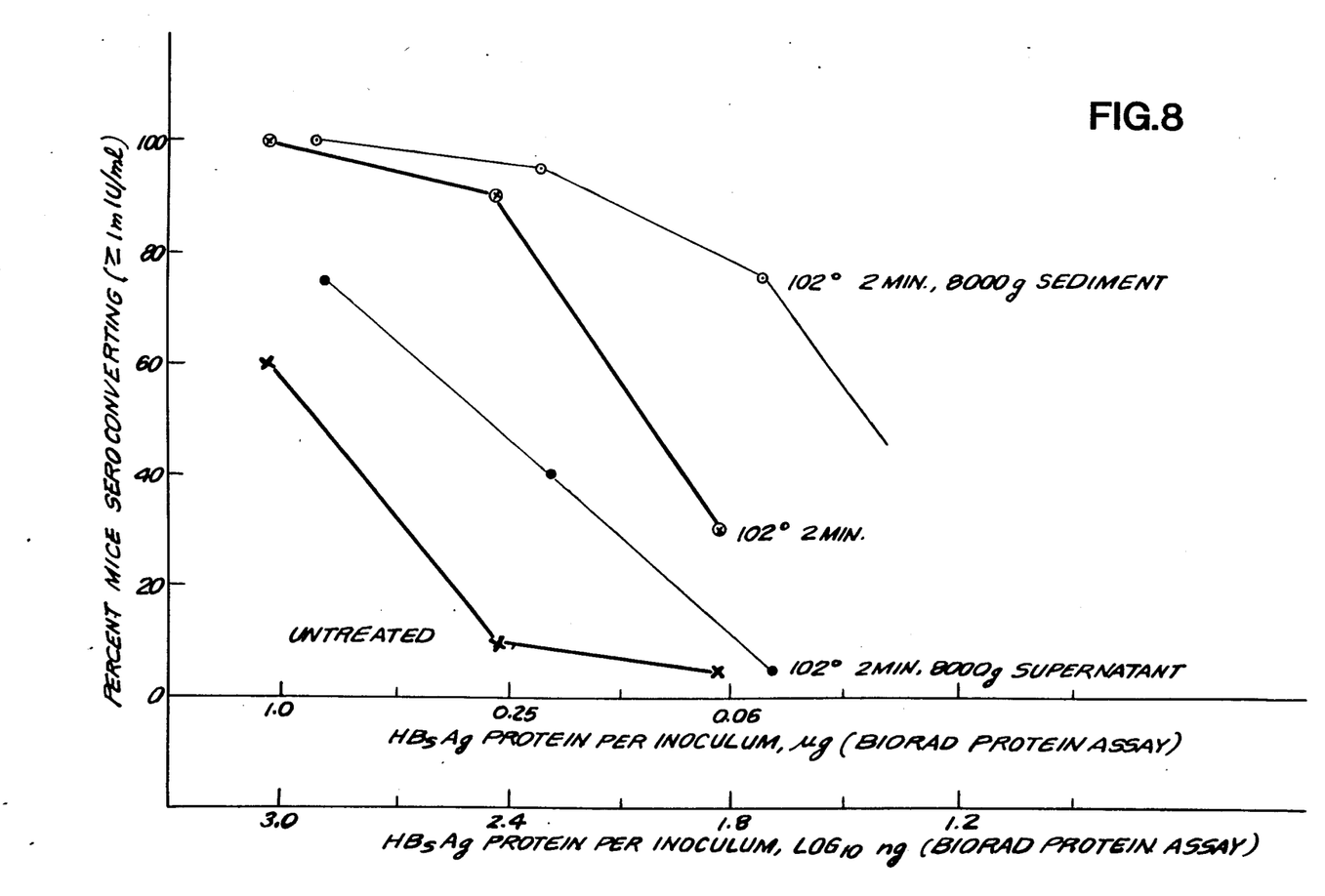
FIG. 8 shows the effect of heat inactivation on immunogenicity of purified HBsAg in mice of the preparations whose morphology was illustrated in FIGS. 3–6.

FIG. 8 shows the percent of mice developing at least 1 mIU/ml of anti-HBs 28-30 days after a single injection of dilutions of the four preparations. The heat treated preparation is seen to have a markedly enhanced immunogenicity by this criterion. Estimation of the dose required to seroconvert 50% of the mice reveals that heat treatment results in a 7.4 fold potentiation of immunogenicity, as revealed by the data of Table 2 below. The filamentous fraction (Example 5) was the most immunogenic, with a 29.5 fold potentiation.

TABLE 1

Effect of Heating on Specific Antigenicity

| Example | Material | HBsAg Protein[1] (mg/ml) | HBsAg Antigenicity[2] (mg/ml) | Specific Antigenicity[3] | |
|---|---|---|---|---|---|
| | | | | | % of original |
| 2 | Untreated HBsAg | 1.44 | 0.55 | 0.38 | 100 |
| 3 | 102° C. 2 min Rx HBsAg | 1.44 | 0.27 | 0.19 | 50 |
| 4 | 102° C. 2 min 8000 g supernatant | 0.74 | 0.23 | 0.31 | 81 |
| 5 | 102° C. 2 min 8000 g sediment | 0.35 | 0.02 | 0.06 | 16 |

[1]By BIORAD Protein Assay
[2]By parallel line radioimmunoassay (RIA) using AUSRIA Tests in comparison to FDA provisional HBsAg/ad standard.
[3]Specific Antigenicity: μg HBsAg by RIA vs. HBsAg/ad standard/μg HBsAg protein by BIORAD Protein Assay.

TABLE 2

EFFECT OF HEAT INACTIVATION OF PURIFIED HBsAg ON IMMUNOGENICITY IN MICE: SUMMARY

| EXAMPLE | MATERIAL | $Log_{10}$ng/mouse | ng/mouse | POTENTIATION FACTOR |
|---|---|---|---|---|
| | (A) EFFECT ON DOSE REQUIRED FOR 50% SEROCONVERSION ($ED_{50}$) | | | |
| | | ESTIMATED $ED_{50}$ | | |
| 2 | Untreated HBsAg | 2.91 | 813 | 1.0 |
| 3 | 102° C. 2 min Rx HBsAg | 2.04 | 110 | 7.4 |
| 4 | 102° C. 2 min 8000 g supernatant | 2.46 | 288 | 2.8 |
| 5 | 102° C. 2 min 8000 g sediment | 1.44 | 27.6 | 29.5 |
| | (B) EFFECT ON MEAN ANTI-HBs LEVELS IN RESPONDERS | | | |
| | | ESTIMATED DOSE GIVING 1.5 $Log_1$mIU/ml | | |
| 2 | Untreated HBsAg | 3.18 | 1500 | 1.0 |
| 3 | 102° C. 2 min Rx HBsAg | 2.40 | 250 | 6.0 |
| 4 | 102° C. 2 min 8000 g supernatant | 2.46 | 288 | 5.2 |
| 5 | 102° C. 2 min 8000 g sediment | 1.95 | 89 | 16.8 |

From the data above, it is concluded that heating of substantially pure HBsAg particles obtained by the separation procedure described above actually increases the immunogenicity of the HBsAg so that higher antibody levels are provided. A quantitative parameter is derived by estimating the dose required to produce a geometric mean anti-HBs level of 1.5 $Log_{10}$ mIU/ml (32 mIU). Using this parameter, heating at 102° C. for 2 minutes is estimated to increase immunogenicity 6-fold. Thus, the proteinaceous masses of the invention can be characterized as having an immunogenicity 4 to 10 fold, preferably 6 to 8 fold greater than the immunogenicity of a proteinaceous mass consisting essentially of spherical HBsAg particles of 18-24 nm in diameter. Of course, by separating the filamentous structures of the invention from the spherical 18-24 nm particles, the resultant composition can have an even greater enhanced immuonogenicity on the order of 20 to 30 fold, as evidence by the data supra in respect of the composition of Example 5.

Thus, it was surprisingly found that by inactivating HBsAg purified by the route of the invention at 102° C. for 2 minutes as described not only did the residual infectivity drop as was intended, but a dramatic increase in immunogenicity was unexpectedly obtained. This enhanced immunogenicity permits the formulation of vaccine of lower protein content and, thus, reduces the overall cost of the vaccine's production so that it is well below that of currently available vaccines.

EXAMPLE 8

Comparative Evaluation of Heat Inactivated Vaccine obtained by another Purification Technique and similar, but different Heat Inactivation Technique with Inactivation of Purified Antigen Obtained by the Steps of this Invention HBsAg was purified by the procedure described supra by precipitation twice with polyethylene glycol followed by purification by negative adsorption to hydroxylapatite and submitted to purification by isopynic centrifugation. This partially purified material is identified herein as Sample A.

Another partially purified HBsAg composition, identified herein as Sample B, was made by the method described by Brummelhuis et al (preparation of Hepatitis B Vaccine by Heat Inactivation in *Hepatitis B Vaccine*, in Serum Symposium No. 18., Eds. P. Maupas and P. Guesry, Elsevier/North-Holland Biomedical Press, 1981)

Sample A was diluted with phosphate buffered saline to 1 mg/ml, 2 mg/ml, 4 mg/ml and 6 mg/ml and subjected to heat treatment as described below. Sample B was subjected to the heat treatment using the resuspended final pellet of HBsAg adjusted to a concentration of 20 ug HBsAg/ml as specified by the Brummelhuis procedure.

Samples A and B were placed into metal tubing with an internal diameter of 2 mm, extended with a short length of silicon rubber tubing, sealed with metal screw clamps. Heat inactivation was accomplished by immersing the tubes into a thermo stabilized oil bath heated to 102° C. The residence time of Samples A and B while at a temperature of 102° C. was two minutes. Thereafter, they were transferred to an ice water bath for cooling.

Samples of the resultant products were subjected to electron microscopy after negative staining in the same manner as FIG. 3 through 6, i.e., with phosphotungstic acid negative stain. The electron micrograph of Samples A (1–6 mg/ml) revealed the same polymorphic filaments shown in FIGS. 4 through 6. The inactivated sample prepared according to the procedure of the Netherlands Red Cross, Sample B, contained in addition to HBsAg at least about 3 mg/ml of other serum proteins. The electron microscopy photograph thereof revealed substantially no filamentous particles of HBsAg. It has been found that addition of sodium caprylate stabilized albumin in 1–3 mg/ml, as in Example 6, does not alter the transformation to the polymorphous forms (FIG. 7), or the enhancement of immungenicity. It was concluded that the manner by which the HBsAg is purified as well as the concentration at which it is heated, determines of whether upon subsequent flash heat treatment, the HBsAg particles are converted into the novel and unusual morphological forms shown in FIGS. 4 through 6. Thus, heat inactivation is not per se determinative of the morphological effect, but rather the novel morphological forms which account for the improved immunogenicity result from a combination of the purification technique and actual heat inactivation procedure used.

The foregoing describes the best mode presently contemplated for carrying out the invention. In initial studies which gave rise to the unusual morphological forms of HBsAg, the purified HBsAg was diluted with a compatible protein, e.g., serum albumin to guard against any deleterious effects that the heat inactivation might have on the HBsAg, i.e., to protect the same against denaturation. The present invention is based on the discovery that inactivation could be carried out without this dilution and, thus, the preferred mode of carrying out the invention is to effect the inactivation upon purified and undiluted HBsAg.

We contemplate that the principles of this invention, i.e., enhancement of immunogenicity of a lipid membrane immunogen by flash heat inactivation of highly concentrated purified membrane preparations will be readily applicable to the enhancement of the effectiveness, and/or reduction in required dose, of other vaccines such as recombinant DNA derived vaccines produced in eukaryotic cells, e.g., yeast or cell culture derive recombinant DNA based hepatitis B and other vaccines, as well as present killed vaccines such as that for influenza, rabies, rubeola, herpes group viruses, retroviruses such as HTLV I, II and III, parasitic vaccines and others now available or in the process of development.

What is claimed is:

1. In a process for heat inactivating a virus in a concentrated mass containing the same and antigenic components thereof, the improvement wherein the concentrated mass is subjected to said heat inactivation without dilution thereof by a proteinaceous material, said heat inactivation comprising subjecting the mass to a temperature of 101° to 104° C. for a dwell time of 1 to 15 minutes.

2. A process according to claim 1 wherein said concentrated mass is undiluted by any stabilizing material.

3. A process according to claim 1 wherein said concentrated mass is obtained from serum containing said virus by removal of other serum proteins.

4. A process according to claim 3 wherein the steps of forming said concentrated mass by removal of other serum proteins is effected without dilution of the virus containing mass by any protein.

5. A process according to claim 3 wherein the heat inactivation is effected upon a concentrated mass whose antigenic containing particles are present in an amount of at least 0.5 mg/ml.

6. A process according to claim 1 wherein following the heat inactivation, the concentrated mass is thereafter cooled.

7. A process according to claim 6 wherein the HBsAg containing particles have been obtained by:
   A. precipitating HBsAg from blood plasma by contacting the same with polyethylene glycol to separate HBsAg from other serum proteins contained therein;
   B. effecting negative adsorption of separated HBsAg on hydroxylapatite;
   C. subjecting the so adsorbed HBsAg isopynic centrifugation.

8. A process according to claim 7 wherein the particles are heated in a tube of diameter 0.1 to 10 mm with the tube suspended in a heating medium for between 1 and 15 minutes at 101° to 104° C. at a pressure of 800 to 1000 mm Hg.

9. A proteinaceous mass produced by the process of claim 1.

10. A proteinaceous mass produced by the process of claim 6.

11. A proteinaceous mass produced by the process of claim 7.

12. A process according to claim 1, wherein the dwell time is 2 to 5 minutes.

13. A process according to claim 5, wherein the antigenic containing particles are HBsAg particles.

14. A process according to claim 5, wherein the antigenic containing particles are present in a concentration of 0.5 to 10 mg/ml.

15. A process according to claim 1, wherein the mass contains at least 95% by weight HBsAg containing particles.

16. A process according to claim 1, wherein the mass contains at least 99% by weight HBsAg containing particles.

17. A process according to claim 1, wherein said heat inactivation is conducted at a pressure of 800 to 1000 mm Hg.

18. A process according to claim 1, wherein said heat inactivation is conducted at a pressure of 900 to 1000 mmm Hg.

* * * * *

UNITED STATES PATENT AND TRADEMARK OFFICE
CERTIFICATE OF CORRECTION

PATENT NO. : 4,695,454

DATED : September 22, 1987

INVENTOR(S) : Alfred M. Prince, et al.

It is certified that error appears in the above-identified patent and that said Letters Patent is hereby corrected as shown below:

Abstract, penultimate line — Delete "5 minutes" and substitute --15 minutes--

Col. 4, line 30 — After "schematic" insert --diagram--

Col. 5, line 6 — Correct spelling of --isopycnic--

Col. 5, line 13 — After "minutes" insert --,--

Col. 11, line 1 — Correct --Preparation--

Signed and Sealed this

Third Day of May, 1988

Attest:

Attesting Officer

DONALD J. QUIGG

Commissioner of Patents and Trademarks